(12) United States Patent
Prutchi et al.

(10) Patent No.: US 6,587,721 B1
(45) Date of Patent: Jul. 1, 2003

(54) TRIGGER-BASED REGULATION OF EXCITABLE TISSUE CONTROL OF THE HEART

(75) Inventors: David Prutchi, Lake Jackson, TX (US); Yuval Mika, Zichron Yaakoc (IL); Ziv Belsky, Haifa (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

(21) Appl. No.: 09/831,282

(22) PCT Filed: Nov. 4, 1999

(86) PCT No.: PCT/IL99/00592
§ 371 (c)(1),
(2), (4) Date: Sep. 10, 2001

(87) PCT Pub. No.: WO00/27472
PCT Pub. Date: May 18, 2000

Related U.S. Application Data

(60) Provisional application No. 60/107,479, filed on Nov. 6, 1998.

(30) Foreign Application Priority Data

Mar. 30, 1999 (IL) .................................................. 129257

(51) Int. Cl.$^7$ ............................................. A61N 1/368
(52) U.S. Cl. ......................................................... 607/9
(58) Field of Search ............................. 607/9, 15, 11; 600/526

(56) References Cited

U.S. PATENT DOCUMENTS

| | | | |
|---|---|---|---|
| 4,554,922 A | 11/1985 | Prystowsky et al. | |
| 5,083,564 A | 1/1992 | Scherlag | |
| 5,213,098 A | 5/1993 | Bennett et al. | |
| 5,284,491 A | 2/1994 | Sutton et al. | |
| 5,514,162 A | 5/1996 | Bornzin et al. | |
| 5,626,622 A | 5/1997 | Cooper | |
| 5,755,740 A | 5/1998 | Nappholz | |
| 5,792,198 A | 8/1998 | Nappholz | |
| 5,800,464 A | 9/1998 | Kievel | |
| 5,807,234 A | 9/1998 | Bui et al. | |
| 5,871,506 A | 2/1999 | Mower | |
| 6,292,693 B1 * | 9/2001 | Darvish et al. | 607/9 |
| 6,298,268 B1 * | 10/2001 | Ben-Haim et al. | 607/9 |
| 6,363,279 B1 * | 3/2002 | Ben-Haim et al. | 607/9 |
| 6,411,847 B1 * | 6/2002 | Mower | 607/9 |

FOREIGN PATENT DOCUMENTS

| | | |
|---|---|---|
| WO | WO 97/25098 | 7/1997 |
| WO | WO 98/10832 | 3/1998 |
| WO | WO 00/27476 | 5/2000 |

OTHER PUBLICATIONS

A. Antoni et al., "Polarization Effects of Sinusoidal 50–Cycle Alternating Current on Membrane Potential of Mammalian Cardiac Fibres", *Pflügers Arch.* 314, pp. 274–291, 1970.

A.H. Foster et al., "Acute Hemodyamic Effects of Atrio–Biventricular Pacing in Humans", 1995, *The Society of Thoracic Surgeons* vol. 59, pp. 294–299.

(List continued on next page.)

*Primary Examiner*—Kennedy Schaetzle
(74) *Attorney, Agent, or Firm*—William H. Dippert; Reed Smith LLP

(57) ABSTRACT

A method and apparatus for modifying contractility of heart tissue. The method includes applying electrodes (34, 35, 38) to one or more sites in the heart (20) and making a determination at which of the sites, if any, to pace the heart. A parameter of an excitable tissue control (ETC) signal (50, 60) to be applied to the heart is set responsive to the determination, and the ETC signal is applied to at least one of the electrodes responsive to the parameter, so as to enhance contractility of the heart.

32 Claims, 4 Drawing Sheets

OTHER PUBLICATIONS

S. Cazeau et al., "Multisite Pacing for End–Stage Heart Failure: Early Experience", *Pacing and Clinical Electrophysiology* vol. 19, Nov. 1996, Part II, pp. 1748–1757'.

Yu et al., "Does Biventricular Pacing Provide Better Cardiac Function than Univentricular Pacing in Normal Dogs?", Abstract, *Heart Failure Society Abstracts–on–Disk®*, Sep. 13–16, 1998, Boca Raton, Florida, one page.

A. Auricchio et al., "Acute Pacing of the Left Ventricle is Associated with Largest Hemodynamic Improvement in PATH–CHF Heart Failure Patients", Abstract, *Heart Failure Society Abstracts–on–Disk®*, Sep. 13–16, 1998, Boca Raton, Florida, one page.

C. Leclercq et al., "Comparative Effects of Permanent Biventricular Pacing in Class III and Class IV Patients", *Pacing and Clinical Electrophysiology*, Apr. 1998, vol. 21, No. 4, Part II, p. 911.

P. F. Bakker et al., "Beneficial Effects of Biventricular Pacing of Congestive Heart Failure", *PACE*, vol. 17, Apr. 1994, Part II, one page.

P. F. Bakker et al., Biventricular Pacing Improves Functional Capacity in Patients with End–Stage Congestive Heart Failure, *PACE*, Apr. 1995, Part II, p. 825.

U.S. patent application No. 09/276,460 to Yuval Mika et al., entitled "Apparatus and Method for Timing the Delivery of Non–Excitatory ETC Signals to the Heart", filed Mar. 3, 1999.

* cited by examiner

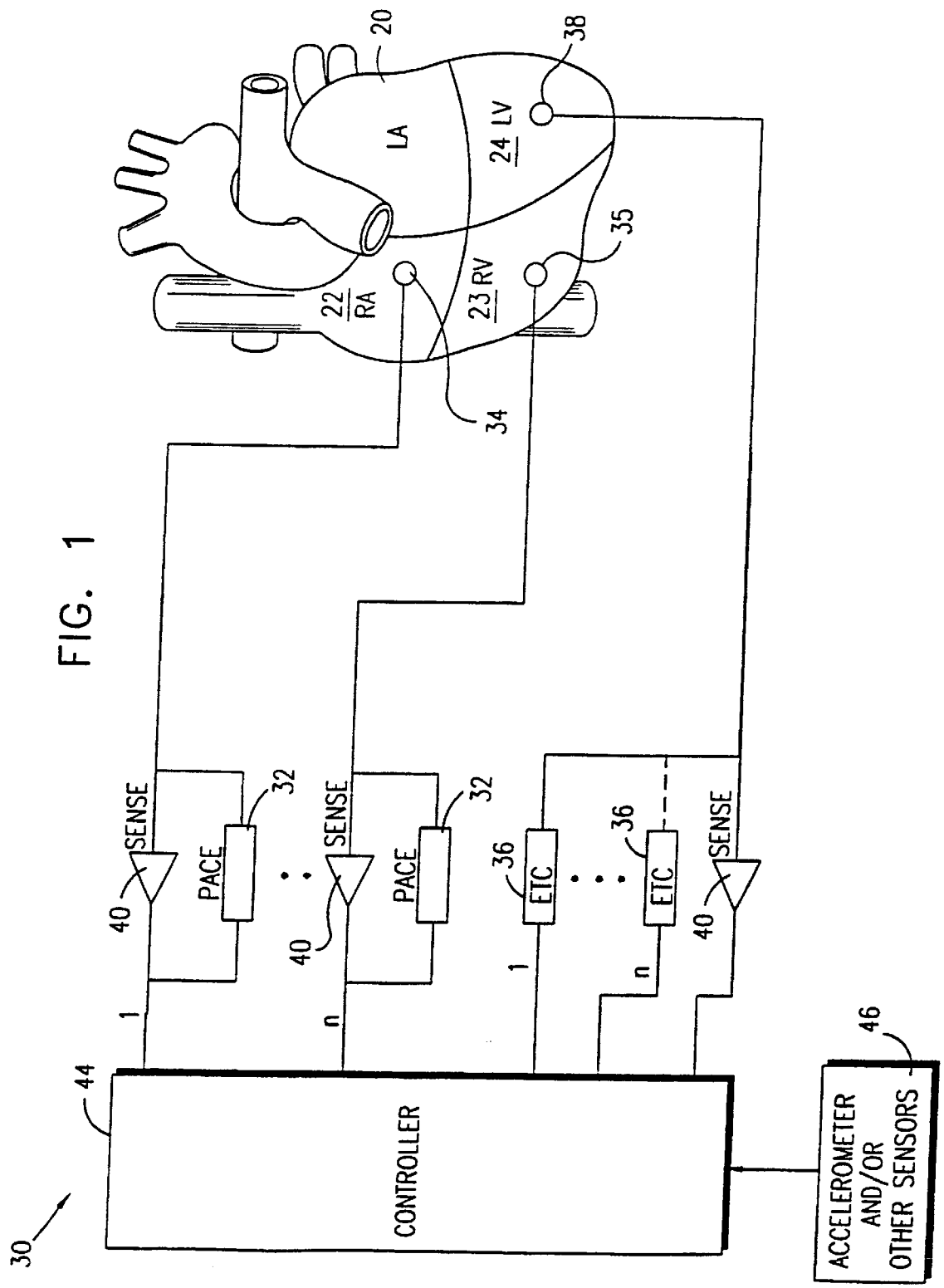

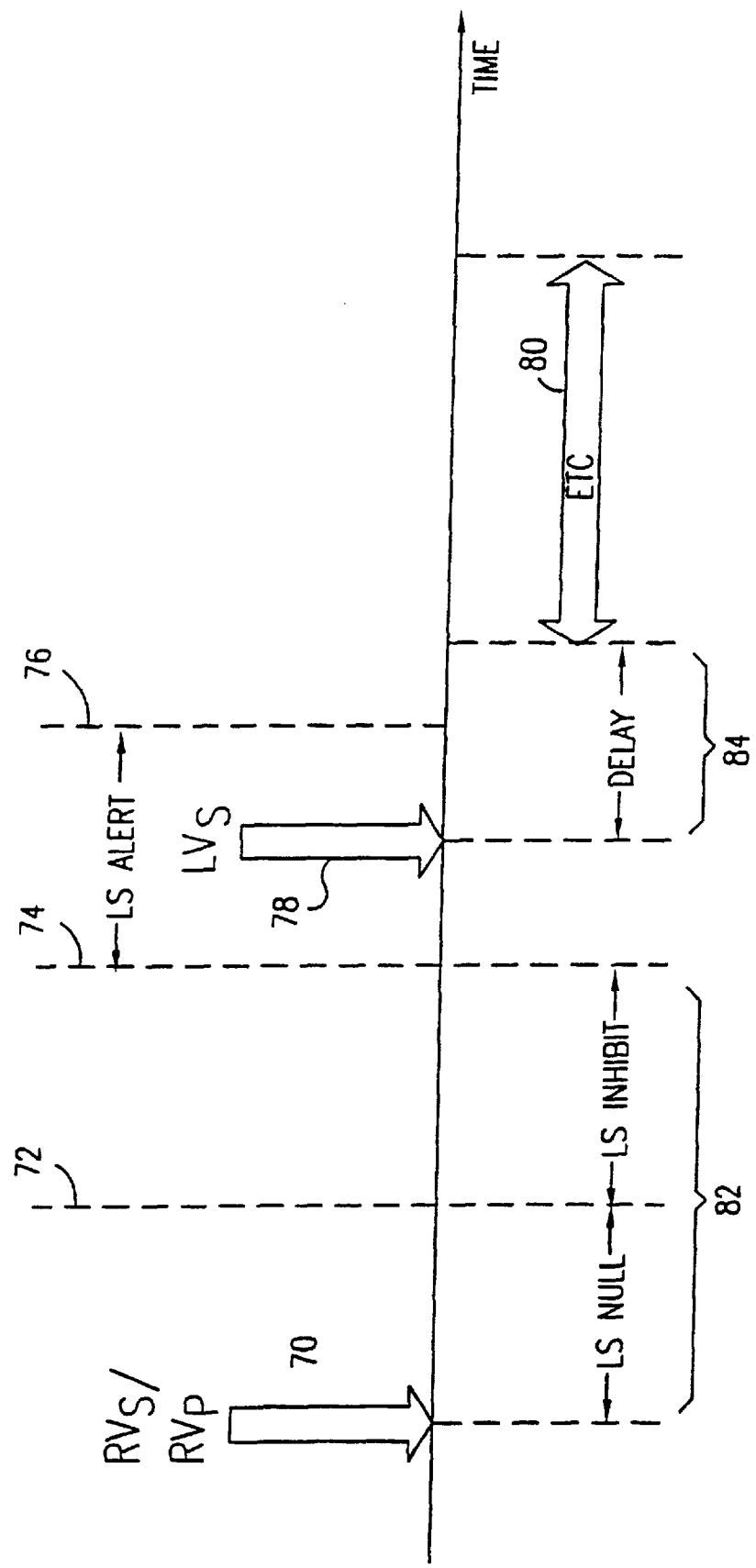

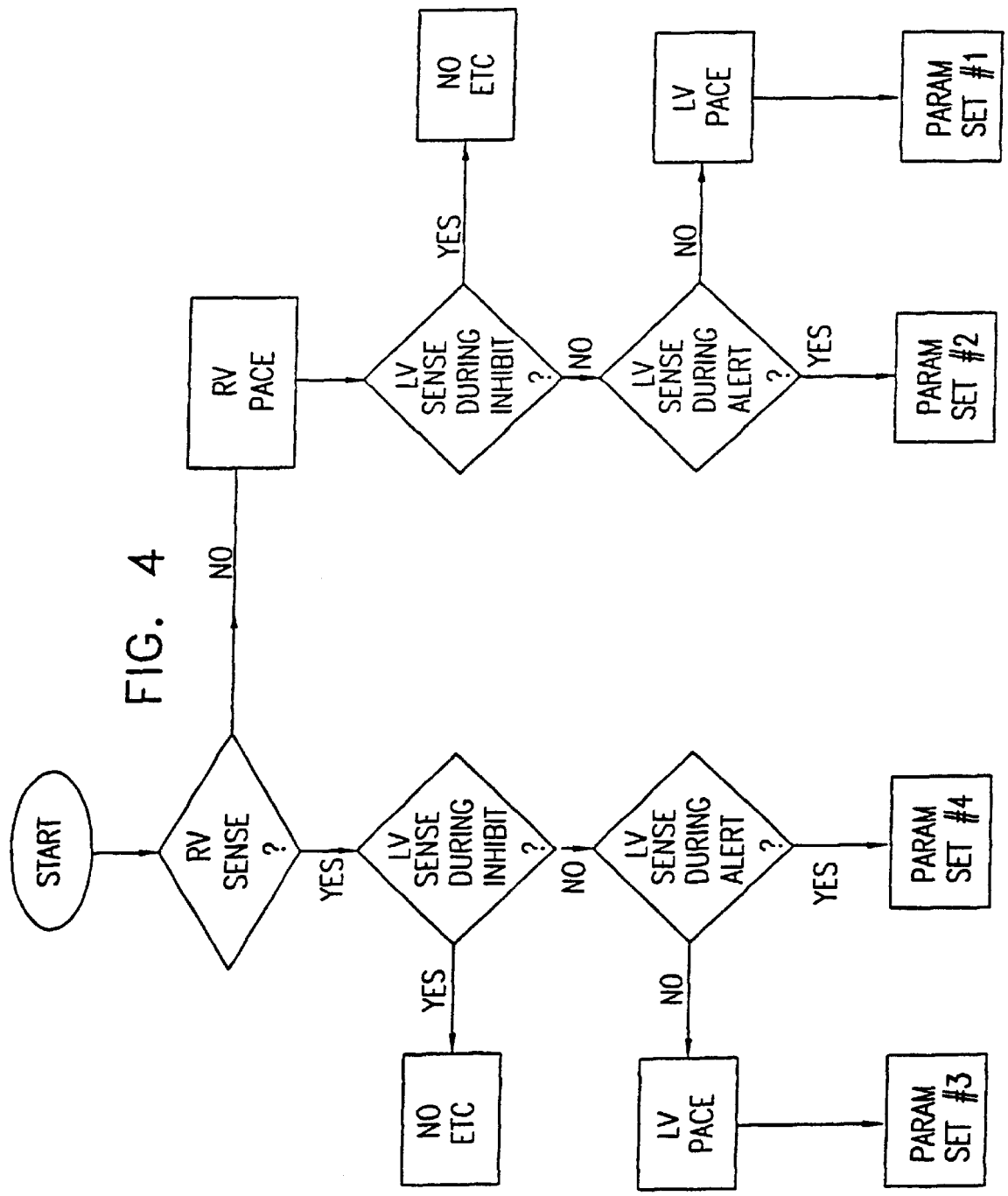

TRIGGER-BASED REGULATION OF EXCITABLE TISSUE CONTROL OF THE HEART

CROSS-REFERENCE TO RELATED APPLICATIONS

This patent application claims the benefit of U.S. Provisional Patent Application No. 60/107,479, filed Nov. 6, 1998 which is assigned to the assignee of the present patent application and is incorporated herein by reference.

FIELD OF THE INVENTION

The present invention relates generally to invasive devices and methods for treatment of the heart, and specifically to devices and methods for pacing and electrical control of the heart muscle.

BACKGROUND OF THE INVENTION

Modern cardiac pacemakers include not only pacing circuits, for generating pulses to pace the heart, but also sensing circuits, for sensing electrical activity in the heart tissue. Such pacemakers are designed to detect activation of the heart tissue due to sinus rhythm and generally to apply the pacing pulses only when appropriate intrinsic activation of the heart tissue does not occur.

U.S. Pat. No. 5,213,098, which is incorporated herein by reference, describes a pacing device that applies paired or triggered stimulation pulses in order to induce post-extrasystolic potentiation (PESP). The paired pulse is applied when the heart is paced, whereas the triggered pulse is applied when the heart is in sinus rhythm. The device is typically used to stimulate the right atrium in order to augment filling of the ventricles. One or more sensors are used to monitor physiological indicators of cardiac performance and stress. Signal processing circuitry varies a parameter of the stimulation, such as the frequency or number of heart cycles between periodic delivery of the pulses, dependent on the physiological indicators.

PCT patent application PCT/IL97/00012, published as WO 97/25098, to Ben-Haim et al., which is incorporated herein by reference, describes methods for modifying the force of contraction of at least a portion of a heart chamber by applying a non-excitatory electrical signal to the heart at a delay after electrical activation of the portion. In the context of the present patent application, the use of such a non-excitatory signal is referred to as Excitable Tissue Control (ETC). The non-excitatory signal may be applied in combination with a pacemaker or defibrillator, which applies an excitatory signal (i.e., pacing or defibrillation pulses) to the heart muscle.

SUMMARY OF THE INVENTION

It is an object of some aspects of the present invention to provide improved methods and apparatus for pacing of the heart together with Excitable Tissue Control (ETC) so as to modify or control hemodynamic performance of the heart under conditions of both paced and intrinsic cardiac rhythm.

In preferred embodiments of the present invention, an electrical cardiac stimulator comprises one or more pacing and/or sensing electrodes and one or more ETC electrodes, which are placed at respective sites in one or more chambers of the heart. An electrical control unit receives signals, preferably from the pacing and/or ETC electrodes, or alternatively, from dedicated sensing electrodes, indicative of electrical activation in the heart tissue. Responsive to the received signals, the control unit determines whether to pace the heart and, as appropriate, selects a suitable pacing mode and applies pacing pulses to the electrodes in accordance with the selected mode. The control unit sets parameters for ETC signals to be applied to the heart, dependent on whether the heart is paced and responsive to the selected pacing mode and pacing sites. The signals are applied to the ETC electrodes in accordance with the parameters, so as to provide optimal enhancement of contractility and reduced risk of arrhythmogenic effects of the ETC signals.

In some preferred embodiments of the present invention, the pacing and/or sensing electrodes are placed in the right atrium and right ventricle of the heart, and the ETC electrodes are placed in the left ventricle of the heart. The structure and function of the control unit and the placement of and signals applied to the electrodes are, preferably, generally as described in the above-mentioned U.S. Provisional Patent Application No. 60/107,479. The selection of ETC parameters is preferably dependent upon whether the heart is in sinus rhythm, or whether the heart is paced only in the right atrium, or in the right and/or left ventricle, as well. Further preferably, the ETC signals are applied responsive to a trigger, wherein the source of the trigger depends upon which site or sites are paced and from which sites the circuitry receives the signals indicative of tissue activation.

The parameters that are selected and varied by the circuitry preferably include timing parameters, particularly a duration of the ETC signals and a delay of the signals relative to the trigger. Selection of the timing parameters on this basis reflects differences in the propagation time and propagation paths of intrinsic electrical activation impulses in the heart as opposed to activation due to pacing. Alternatively or additionally, other signal parameters may be varied, including the voltage, current, duration, polarity, shape and frequency of the ETC signal waveform. Further alternatively or additionally, the duration and/or delay of the ETC signals is varied responsive to the heart rate, whether intrinsic or paced.

PCT patent application PCT/IL97/00236, and the corresponding U.S. patent application Ser. No. 09/254,900, which are assigned to the assignee of the present patent application and whose disclosures are incorporated herein by reference, also describe a pacemaker that gives cardiac output enhancement. This pacemaker applies both excitatory (pacing) and non-excitatory (ETC) electrical signals to the heart. By applying non-excitatory signals of suitable strength, appropriately timed with respect to the heart's electrical activation, the contraction of selected segments of the heart muscle can be increased or decreased, thus increasing or decreasing the stroke volume of the heart.

There is therefore provided, in accordance with a preferred embodiment of the present invention, a method for modifying contractility of heart tissue, including:
  applying electrodes to one or more sites in the heart;
  making a determination at which of the sites, if any, to pace the heart;
  setting a parameter of an excitable tissue control (ETC) signal to be applied to the heart responsive to the determination; and
  applying the ETC signal to at least one of the electrodes responsive to the parameter, so as to enhance contractility of the heart.

Preferably, applying the ETC signal includes applying an electrical pulse, and setting the parameter includes setting a delay after which the pulse is to commence. Further preferably, setting the parameter includes assigning a trigger with respect to which the delay is set, wherein making the determination includes detecting electrical activity in the heart, and wherein assigning the trigger includes triggering responsive to the electrical activity.

Preferably, detecting the electrical activity includes detecting activity at or in a vicinity of the at least one of the electrodes to which the ETC signal is applied. Alternatively or additionally, detecting the electrical activity includes detecting activity in the left ventricle of the heart while the heart is paced at one of the electrodes in another chamber of the heart. Further preferably, triggering responsive to the electrical activity includes sensing electrical activation of the tissue and triggering thereon.

In a preferred embodiment, the method includes applying pacing pulses to the heart in accordance with the determination, wherein assigning the trigger includes triggering on one of the pacing pulses. Preferably, triggering on the one of the pacing pulses includes triggering on a pacing pulse applied to the at least one of the electrodes to which the ETC signal is applied. Alternatively or additionally, triggering on the one of the pacing pulses includes triggering on a pacing pulse applied in the left ventricle of the heart.

Preferably, setting the delay includes setting a delay responsive to the determination so as to substantially eliminate the possibility that a new action potential will propagate in the heart tissue responsive to the ETC signal. Additionally or alternatively, setting the delay comprises setting a variable delay responsive to a beat rate of the heart.

Preferably, applying the ETC signal includes applying an electrical waveform, and setting the parameter includes setting a duration of the waveform, wherein setting the duration includes selecting a waveform type and setting the duration responsive to the type. Further preferably, setting the duration includes setting a duration responsive to the determination so as to substantially eliminate the possibility that a new action potential will propagate in the heart tissue responsive to the ETC signal.

Preferably, applying the electrodes includes applying electrodes in two or more chambers of the heart.

There is also provided, in accordance with a preferred embodiment of the present invention, apparatus for modifying contractility of heart tissue, including:

one or more electrodes, which are applied at respective sites in the heart, and an electrical control unit, which makes a determination at which of the sites, if any, to pace the heart, and which sets a parameter of an excitable tissue control (ETC) signal to be applied to the heart responsive to the determination and applies the ETC signal to at least one of the electrodes responsive to the parameter, so as to enhance contractility of the heart.

Preferably, the ETC signal includes an electrical pulse, and the parameter set by the control unit includes a delay after which the pulse is to commence. Further preferably, the control unit sets a trigger with respect to which the delay is set, wherein the control unit receives signals from at least one of the electrodes responsive to electrical activity in the heart and sets the trigger based on the electrical activity.

Preferably, the control unit receives the signals from the at least one of the electrodes to which it applies the ETC signal. Alternatively or additionally, the control unit receives the signals from one of the electrodes in the left ventricle of the heart while the heart is paced at another one of the electrodes in another chamber of the heart. Preferably, the control unit senses electrical activation of the tissue and sets the trigger at the time of activation.

In a preferred embodiment, the control unit applies pacing pulses to the heart in accordance with the determination and sets the trigger on one of the pacing pulses. Preferably, the control unit sets the trigger on a pacing pulse applied to the at least one of the electrodes to which the ETC signal is applied. Alternatively or additionally, the control unit sets the trigger on a pacing pulse applied in the left ventricle of the heart.

Preferably, the control unit sets the delay so as to substantially eliminate the possibility that a new action potential will propagate in the heart tissue responsive to the ETC signal. Additionally or alternatively, the control unit varies the delay responsive to a beat rate of the heart.

Further preferably, the ETC signal applied by the control unit includes an electrical waveform, and wherein the parameter set by the control unit includes a duration of the waveform, wherein the control unit selects a waveform type and sets the duration responsive to the type. Preferably, the control unit sets the duration responsive to the determination so as to substantially eliminate the possibility that a new action potential will propagate in the heart tissue responsive to the ETC signal.

Preferably, the electrodes are applied in two or more chambers of the heart.

The present invention will be more fully understood from the following detailed description of the preferred embodiments thereof, taken together with the drawings in which:

BRIEF DESCRIPTION OF THE DRAWINGS

FIG. 1 is a schematic illustration of an Excitable Tissue Control (ETC) device applied to a heart, in accordance with a preferred embodiment of the present invention;

FIG. 3 is a schematic timing diagram illustrating considerations in timing the application of ETC signals to the heart; and FIG. 4 is a flow chart, which schematically illustrates a decision tree for selecting ETC signal pulse parameters, in accordance with a preferred embodiment of the present invention.

DETAILED DESCRIPTION OF PREFERRED EMBODIMENTS

Figure 2A:
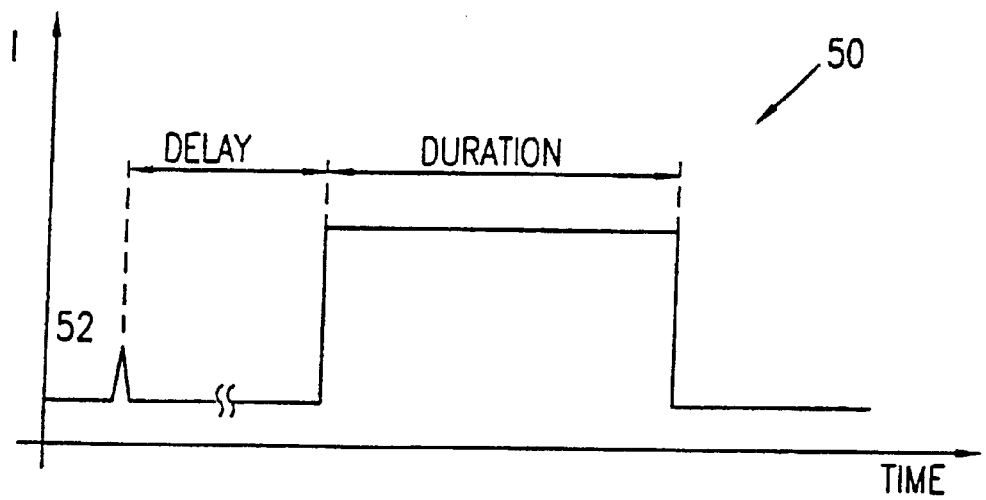
FIGS. 2A and 2B schematically illustrate waveforms of ETC signals applied using the device of FIG. 1, in accordance with a preferred embodiment of the present invention.

Reference is now made to FIG. 1, which is a schematic illustration showing an ETC signal delivery device 30, which is applied to pace and generate ETC signals for application to a heart 20, in accordance with a preferred embodiment of the present invention. Details of the design and construction of devices such as device 30 are provided in the above-mentioned U.S. and PCT patent applications.

Device 30 comprises pacing circuits 32 and ETC circuits 36, which are respectively coupled to drive one or more pacing electrodes 34 and (optionally) 35 and one or more ETC electrodes 38. As shown in FIG. 1, pacing electrodes 34 and 35 are typically applied in right atrium 22 and right ventricle 23, respectively. ETC electrodes 38 are applied to left ventricle 24, most preferably epicardially or intravenously to the free wall of the left ventricle. Greater numbers of electrodes and different electrode placements are also possible.

Sensing circuits 40 receive electrogram signals from heart 20, which signals are preferably provided by the pacing and/or ETC electrodes (although separate sensing electrodes can also be used for this purpose). Control circuitry 44, preferably comprising a microprocessor and a memory, for storing programs and data, receives the signals from sensing circuits 40. Circuitry 44 processes the signals to detect electrical activation in the heart tissue, as well as to derive the heart rate and, optionally, other parameters relating to cardiac function. Depending on detection of the electrical activation, circuitry 44 decides whether it is necessary to pace heart 20 and, if pacing is needed, actuates pacing circuits 32 accordingly. ETC circuits 36 can also be controlled to pace left ventricle 24 by applying suitable pacing signals through one or more of electrodes 38. Preferably, an accelerometer or other sensor 46 provides signals to circuitry 44 responsive to motion, i.e., physical activity of the patient. Other sensors of any suitable type known in the art may also be used. Responsive to the signals from sensing circuits 40 and sensor 46, circuitry 44 controls the application of ETC signals to the heart, as described hereinbelow.

Figure 2B:
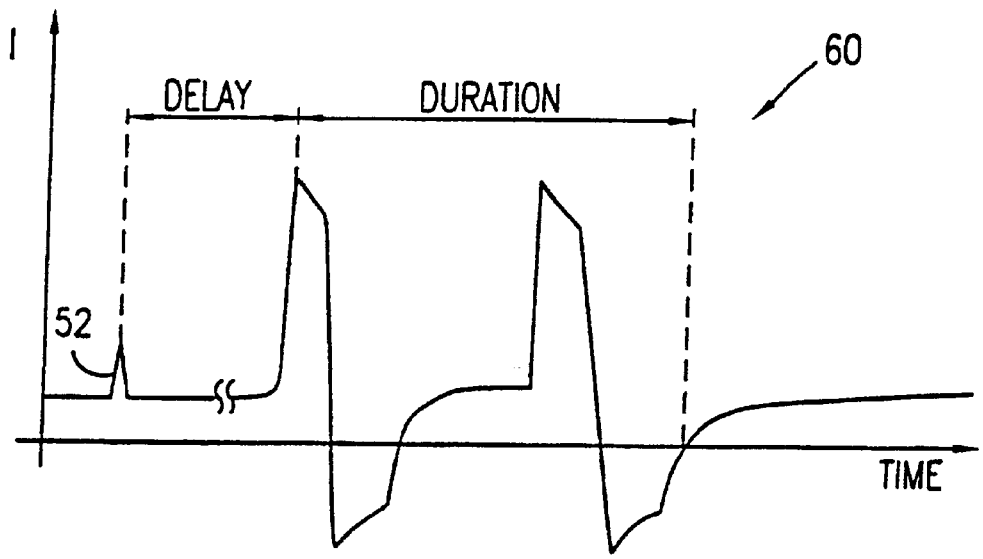

FIGS. 2A and 2B schematically illustrate ETC signal waveforms 50 and 60, respectively, which are applied by circuitry 44 to ETC electrodes 38, in accordance with preferred embodiments of the present invention. Waveforms 50 and 60 are shown for purposes of illustrating certain signal parameters that are controlled by circuitry 44. It will be understood, however, that the principles of the present invention may similarly be applied to the control of other signal parameters and using waveforms of other types and shapes.

As shown in FIG. 2A, waveform 50 comprises a square wave pulse having a given duration, and which is applied at a given delay following a trigger 52. The trigger preferably corresponds to a time at which circuitry 44 determines that activation has occurred at the site of one of electrodes 38, based on signals received from the electrode via sensing circuits 40. Alternatively, the trigger corresponds to the time at which a pacing pulse is applied to one of the electrodes. As described hereinbelow, circuitry 44 selects the trigger source based on predetermined decision criteria, and sets the values of the delay and duration of waveform 50 based, inter alia, on the trigger source. The amplitude of waveform 50 is given in units of current (I) and is typically in the range of about 5 to 30 mA.

Waveform 60, shown in FIG. 2B, comprises a biphasic pulse train. The delay of waveform 60 relative to trigger 52 and the duration of the waveform are controlled in a manner similar to that applied to control waveform 50. The duration of waveform 60 as defined herein corresponds to the overall duration of the pulse train. It is noted that circuitry 44 may also control the pulse shape, width, phase, frequency and other parameters with respect to the individual pulses making up the waveform.

FIG. 3 is a timing diagram illustrating a sequence of timing windows used in controlling the application of ETC waveforms to the heart, in accordance with a preferred embodiment of the present invention. The durations of the successive timing windows are chosen so that the ETC signal is administered at an optimal time, most preferably set so as to substantially eliminate the possibility that a propagating action potential will be generated responsive to the signal. The durations are set by control circuitry 44 based on preprogrammed criteria and, optionally, are varied by the circuitry responsive to the heart rate.

The time of activation of right ventricle 23 (following the activation of right atrium 22, not marked in FIG. 3) is represented in the figure by an arrow 70. The activation may be either be sensed ($RV_s$) using electrode 35, due to natural conduction in the heart tissue, or it may be induced by a pacing pulse ($RV_p$) applied to the electrode, depending on the selected pacing mode and the condition of the patient's heart. Preferably, circuitry 44 applies a pacing pulse to right ventricle 23 when it does not sense natural activation at electrode 35 within a time window whose beginning and end are determined relative to pacing or activation of right atrium 22, as is generally known in the pacing art.

A local sense null period (or window) begins at the time of ventricular activation, indicated by arrow 70, and continues until a time 72, typically 3 to 10 ms later. During this period, any signals received by electrodes 38 from left ventricle 24 are ignored, since they are assumed to be due to artifacts, such as far-field effects of the activation in the right ventricle. A local sense inhibit window follows the end of the null period at time 72 and continues until a time 74. The duration of the inhibit window is typically between 5 and 60 ms, depending, for example, on the positions of the electrodes in the heart, on the heart rate, and on whether or not the right ventricle is paced, as described further hereinbelow. During the inhibit window, signals received by electrodes 38 are no longer considered to be artifactual, but may be due to abnormal activation events in the heart. For this reason, whenever signals above a predetermined threshold are received during the inhibit window, the ETC signal is preferably not applied.

The LS null and LS inhibit windows together make up an interval 82, whose duration may optionally depend on the heart rate, as noted hereinabove. Such rate dependence is desirable because under normal physiological conditions, conduction velocity of cardiac tissue increases with the heart rate. Preferably, interval 82 is adaptively controlled, relative to a preprogrammed pacing interval and to the V—V interval (inverse of the heart rate), so that the interval decreases with increasing heart rate in accordance with the following formula:

Interval 82=Programmed interval*{1−factor*(programmed pacing period−V—V interval)/programmed pacing period}

The "factor" is a constant, which is preferably adjustable in a range between 50% and 150%.

At time 74, a local sense alert window is opened, during which circuitry 44 is prepared to receive signals from electrodes 38 indicative of activation of left ventricle 24 and to initiate the ETC signal based on the activation. When such a signal ($LV_s$) is received, as indicated in FIG. 3 by an arrow 78, it triggers the start of a delay timer, acting as trigger 52 of FIGS. 2A and 2B. At the end of the timer delay 84, an ETC signal, indicated by an arrow 80, is applied. Alternatively, if no activation is sensed at electrodes 38 during the local sense alert window, i.e., before a time 76 marking the end of the window, typically occurring 10–30 ms after time 74, a pacing pulse is preferably applied to the left ventricle. Further alternatively, the left ventricle may be paced without attempting to sense the activation. In such cases, the delay timer is triggered to start from the time of delivery of the pacing pulse to electrodes 38, i.e., the pacing pulse serves as trigger 52. Delay 84 applied by the delay timer and the duration of the ETC signal depend on whether one or both of the right and left ventricles are paced, as described in detail hereinbelow.

Optionally, the duration of delay 84 is varied adaptively responsive to the heart rate, in a manner similar to the variation of interval 82 described above. Preferably, the delay decreases with increasing heart rate, relative to a preprogrammed delay, according to the following formula:

Delay 84=Programmed delay*{1−factor*(programmed pacing period−V—V interval)/programmed pacing period}

As in the case of interval 82, the multiplicative factor in the formula is preferably set to a value in the range between 50% and 150%.

Further aspects of "windowing" in relation to control of the application of pacing and ETC signals to the heart are described in U.S. patent application Ser. No. 09/276,460, which is assigned to the assignee of the present patent application and incorporated herein by reference.

FIG. 4 is a flow chart that schematically illustrates a decision tree for selecting ETC signal parameters, in accordance with a preferred embodiment of the present invention. As described above and as the figure indicates, circuitry 44 selects a source for trigger 52 dependent on whether or not the left ventricle is paced:

If pacing pulses are applied to left ventricle 24, trigger 52 corresponds to application of the left ventricle pacing pulse, as described in the above-mentioned U.S. provisional patent application.

If left ventricle 24 is not paced, but rather the activation potential is sensed in the left ventricle by one or more of electrodes 38, trigger 52 preferably corresponds to the time at which the left ventricular activation is sensed (indicated by arrow 78 in FIG. 3).

Typically, no ETC signal is delivered to the left ventricle in the absence of both pacing and sensing of activation, because of the danger that such a signal could cause ventricular arrhythmia if applied when the heart tissue is not refractory. It may be possible under some conditions, however, to trigger the ETC signal on a pacing pulse applied to another chamber of the heart, such as the right ventricle, or an activation potential sensed therein.

Besides choosing the trigger source, circuitry 44 adjusts ETC signal parameters, including particularly the delay and duration of the signal waveform, responsive to selection of the trigger source and operating mode or device 30. A key aspect of the operating mode is the choice of the pacing site or sites among left ventricle 24, right ventricle 23, and right atrium 22. Table I below illustrates exemplary values of the delay and duration of the ETC signal waveform, dependent on the operating mode and trigger source. These values are listed by way of example, and it will be understood that different values may be found to be appropriate under different circumstances. Generally, the optimal delay and duration will differ from patient to patient based on physiological conditions, such as parameters of conduction in the heart, and will further vary with heart rate, as described hereinabove. The delay and duration values belong to parameter sets #1 through #4 as indicated in FIG. 3, and also depend on the waveform type (square wave 50 or pulse train 60, or other waveform types):

TABLE I

| Param. set | Mode | Trig. source | Waveform delay 84 | Waveform duration Square wave 50 | Waveform duration Pulse train 60 |
|---|---|---|---|---|---|
| #1 | LV pace, RV pace | LV pace | 30–80 ms | 10–50 ms | 10–40 ms |
| #2 | LV sense, RV paced | LV sense | 20–60 ms | 10–50 ms | 10–30 ms |
| #3 | LV pace, RV sense | LV pace | 20–80 ms | 10–50 ms | 10–40 ms |
| #4 | LV sense, RV sense | LV sense | 10–50 ms | 10–40 ms | 10–30 ms |

As the above table shows, each parameter set includes a range of values of delay and duration, which are chosen to provide maximal enhancement of cardiac contractility while minimizing arrhythmogenic effects of the ETC signal. For example, when left ventricle 24 is paced through ETC electrode 38, the activation signal will propagate from the pacing site to the rest of the left ventricle, which will therefore not be receptive to a new propagating action potential for a period of at least 80–100 ms thereafter. For this reason, in parameter sets #1 and #3, the combined duration of the delay and the ETC signal can be relatively long. The durations of the pulse train and square wave signals differ on account of the differing effects that the two types of signals have on cardiac tissue, particularly in terms of possible arrhythmogenic tendencies.

When left ventricle 24 is not paced, but trigger 52 is determined by an activation wave in the heart tissue, as sensed by circuits 40 coupled to electrode 38 in the left ventricle, parameter set #2 and #4 are used. The delay in parameter set #2 is relatively greater than that in parameter set #4 because when the right ventricle is paced (set #2), activation of the left ventricle is relatively slower, since impulses are conducted from the right ventricle mainly through heart muscle tissue, rather than through specialized conduction fibers.

It will be understood that the parameter ranges shown in Table I are representative examples only, and that other ranges may be used within the framework of the principles of the present invention. The ranges shown in the figure comprise empirical values, based on the inventors' clinical and experimental experience with ETC signals to date. The optimal timing and pulse parameters for the ETC waveform within the predetermined ranges depend on the heart rate and other physiological factors, as well as any known conduction problem in the heart. Preferably, in order to set the parameters appropriately for each patient, measurements are made of the actual conduction velocity between the right and left ventricles under both conditions of intrinsic activation (to the extent possible) and pacing in one or both of the ventricles.

During operation of device 30, circuitry 44 preferably receives signals from sensing circuits 40 and sensors 46 indicative of the heart rate, physical exertion and hemodynamics. It uses these signals, most preferably together with patient data stored in the memory of the device, in order to set the exact delay and waveform duration within the predetermined ranges, as well as setting other variable ETC signal parameters.

For any of the operating modes described hereinabove, the intensity of the ETC signal is preferably determined responsive to the heart rate, most preferably as described in Israel Patent Application no. 127,092. Alternatively or additionally, the signal intensity is controlled responsive to input from sensor 46 (or from multiple sensors), as described in Israel Patent Application 127,925. Both of these applications are assigned to the assignee of the present patent application and are incorporated herein by reference. Various signal parameters, such as the current amplitude shown in FIGS. 2A and 2B, contribute to the intensity and may be varied in order to regulate the intensity. Most preferably, a duty cycle of the ETC signal is varied, wherein in the context of the present patent application, the duty cycle is determined by the relative number of times pulses 50 or 60 are applied in a sequence of a given number of trigger pulses 52.

Although the preferred embodiments described above refer mainly to regulation of the duration and delay of the ETC waveform, the principles of the present invention may be applied to control other pulse parameters, such as the voltage, current, duration, polarity, shape and frequency of the signal waveform. It will thus be appreciated that the preferred embodiments described above are cited by way of example, and the full scope of the invention is limited only by the claims.

What is claimed is:

1. A method for modifying contractility of heart tissue, comprising:
applying electrodes to one or more sites in the heart;
making a determination at which of the sites, if any, to pace the heart;
setting a parameter of an excitable tissue control (ETC) signal to be applied to the heart responsive to the determination, and
applying the ETC signal to at least one of the electrodes responsive to the parameter, so as to enhance contractility of the heart.

2. A method according to claim 1, wherein applying the ETC signal comprises applying an electrical pulse, and wherein setting the parameter comprises setting a delay after which the pulse is to commence.

3. A method according to claim 2, wherein setting the parameter comprises assigning a trigger with respect to which the delay is set.

4. A method according to claim 3, wherein making the determination comprises detecting electrical activity in the heart, and wherein assigning the trigger comprises triggering responsive to the electrical activity.

5. A method according to claim 4, wherein detecting the electrical activity comprises detecting activity in a vicinity of the at least one of the electrodes to which the ETC signal is applied.

6. A method according to claim 4, wherein detecting the electrical activity comprises detecting activity in the left ventricle of the heart while the heart is paced at one of the electrodes in another chamber of the heart.

7. A method according to claim 4, wherein triggering responsive to the electrical activity comprises sensing electrical activation of the tissue and triggering thereon.

8. A method according to claim 3, and comprising applying pacing pulses to the heart in accordance with the determination, wherein assigning the trigger comprises triggering on one of the pacing pulses.

9. A method according to claim 8, wherein triggering on the one of the pacing pulses comprises triggering on a pacing pulse applied to the at least one of the electrodes to which the ETC signal is applied.

10. A method according to claim 8, wherein triggering on the one of the pacing pulses comprises triggering on a pacing pulse applied in the left ventricle of the heart.

11. A method according to claim 2, wherein setting the delay comprises setting a delay responsive to the determination so as to substantially eliminate the possibility that a new action potential will propagate in the heart tissue responsive to the ETC signal.

12. A method according to claim 2, wherein setting the delay comprises setting a variable delay responsive to a beat rate of the heart.

13. A method according to claim 1, wherein applying the ETC signal comprises applying an electrical waveform, and wherein setting the parameter comprises setting a duration of the waveform.

14. A method according to claim 13, wherein setting the duration comprises selecting a waveform type and setting the duration responsive to the type.

15. A method according to claim 13, wherein setting the duration comprises setting a duration responsive to the determination so as to substantially eliminate the possibility that a new action potential will propagate in the heart tissue responsive to the ETC signal.

16. A method according to claim 1, wherein applying the electrodes comprises applying electrodes in two or more chambers of the heart.

17. Apparatus for modifying contractility of heart tissue, comprising:
one or more electrodes, which are applied at respective sites in the heart; and
an electrical control unit, which makes a determination at which of the sites, if any, to pace the heart, and which sets a parameter of an excitable tissue control (ETC) signal to be applied to the heart responsive to the determination and applies the ETC stimulation to at least one of the electrodes responsive to the parameter, so as to enhance contractility of the heart.

18. Apparatus according to claim 17, wherein the ETC signal comprises an electrical pulse, and wherein the parameter set by the control unit comprises a delay after which the pulse is to commence.

19. Apparatus according to claim 18, wherein the control unit sets a trigger with respect to which the delay is set.

20. Apparatus according to claim 19, wherein the control unit receives signals from at least one of the electrodes responsive to electrical activity in the heart and sets the trigger based on the electrical activity.

21. Apparatus according to claim 20, wherein the control unit receives the signals from the at least one of the electrodes to which it applies the ETC signal.

22. Apparatus according to claim 20, wherein the control unit receives the signals from one of the electrodes in the left ventricle of the heart while the heart is paced at another one of the electrodes in another chamber of the heart.

23. Apparatus according to claim 20, wherein the control unit senses electrical activation of the tissue and sets the trigger at the time of activation.

24. Apparatus according to claim 19, wherein the control unit applies pacing pulses to the heart in accordance with the determination and sets the trigger on one of the pacing pulses.

25. Apparatus according to claim 24, wherein the control unit sets the trigger on a pacing pulse applied to the at least one of the electrodes to which the ETC signal is applied.

26. Apparatus according to claim 24, wherein the control unit sets the trigger on a pacing pulse applied in the left ventricle of the heart.

27. Apparatus according to claim 18, wherein the control unit sets the delay so as to substantially eliminate the possibility that a new action potential will propagate in the heart tissue responsive to the ETC signal.

28. Apparatus according to claim 18, wherein the control unit varies the delay responsive to a beat rate of the heart.

29. Apparatus according to claim 17, wherein the ETC signal applied by the control unit comprises an electrical waveform, and wherein the parameter set by the control unit comprises a duration of the waveform.

30. Apparatus according to claim 29, wherein the control unit selects a waveform type and sets the duration responsive to the type.

31. Apparatus according to claim 29, wherein the control unit sets the duration responsive to the determination so as to substantially eliminate the possibility that a new action potential will propagate in the heart tissue responsive to the ETC signal.

32. Apparatus according to claim 17, wherein the electrodes are applied in two or more chambers of the heart.

* * * * *